(12) United States Patent
Williamson

(10) Patent No.: US 11,317,798 B2
(45) Date of Patent: May 3, 2022

(54) CATADIOPTRIC UNIT-MAGNIFICATION AFOCAL PUPIL RELAY AND OPTICAL IMAGING SYSTEM EMPLOYING THE SAME

(71) Applicant: NIKON CORPORATION, Tokyo (JP)

(72) Inventor: David M. Williamson, Tucson, AZ (US)

(73) Assignee: NIKON CORPORATION, Tokyo (JP)

( * ) Notice: Subject to any disclaimer, the term of this patent is extended or adjusted under 35 U.S.C. 154(b) by 290 days.

(21) Appl. No.: 16/294,050

(22) Filed: Mar. 6, 2019

(65) Prior Publication Data
US 2019/0261851 A1 Aug. 29, 2019

Related U.S. Application Data

(63) Continuation of application No. PCT/JP2017/031999, filed on Sep. 5, 2017.
(Continued)

(51) Int. Cl.
*A61B 3/10* (2006.01)
*A61B 3/12* (2006.01)

(52) U.S. Cl.
CPC .............. *A61B 3/1025* (2013.01); *A61B 3/10* (2013.01); *A61B 3/102* (2013.01); *A61B 3/12* (2013.01)

(58) Field of Classification Search
CPC ......... A61B 3/1025; A61B 3/10; A61B 3/102; A61B 3/12; G02B 17/02; G02B 17/008; G02B 17/0812; G03F 7/70225
See application file for complete search history.

(56) References Cited

U.S. PATENT DOCUMENTS 4,391,494 A 7/1983 Hershel
4,768,874 A 9/1988 Webb
(Continued)

FOREIGN PATENT DOCUMENTS

DE 4116067 A1 11/1991
EP 2 103 249 A1 9/2009
(Continued)

OTHER PUBLICATIONS

Machine translation of WO-2008037346-A1 (Year: 2008).*
(Continued)

*Primary Examiner* — Darryl J Collins
*Assistant Examiner* — Matthew Y Lee
(74) *Attorney, Agent, or Firm* — Foley & Lardner LLP

(57) ABSTRACT

An optical system configured for imaging an object with the use of two independently-scanning reflectors, the optical system having an optical axis and including: first and second scanning reflectors, the first scanning reflector being configured to scan a beam of light incident thereon in a first plane, the second scanning reflector being configured to scan a beam of light incident thereon in a second plane, and the first and second planes being transverse to one another; and a catadioptric afocal relay system disposed along the optical axis in optical communication with, and between, the first and second scanning reflectors, the catadioptric afocal relay system being configured to image one of the first or second scanning reflectors onto another of the first or second scanning reflectors, in light propagating along the optical axis, with a unit magnification, and the catadioptric afocal relay system including only one reflector.

13 Claims, 12 Drawing Sheets

Related U.S. Application Data

(60) Provisional application No. 62/480,886, filed on Apr. 3, 2017, provisional application No. 62/475,069, filed on Mar. 22, 2017, provisional application No. 62/383,745, filed on Sep. 6, 2016, provisional application No. 62/383,722, filed on Sep. 6, 2016.

(56) References Cited

U.S. PATENT DOCUMENTS

| | | | |
|---|---|---|---|
| 4,893,920 A | 1/1990 | Webb | |
| 4,953,960 A | 9/1990 | Williamson | |
| 5,673,135 A | 9/1997 | Yoshino | |
| 5,815,242 A | 9/1998 | Anderson | |
| 5,883,703 A | 3/1999 | Knirck | |
| 5,991,090 A | 11/1999 | Strahle | |
| 7,573,655 B2 | 8/2009 | Shafer | |
| 7,959,290 B2 | 6/2011 | Cairns | |
| 8,830,590 B2 | 9/2014 | Stites | |
| 9,204,791 B2 * | 12/2015 | Saito | A61B 3/12 |
| 9,259,152 B2 | 2/2016 | Seesselberg | |
| 9,474,447 B2 | 10/2016 | Schmidtlin | |
| 2008/0117532 A1 * | 5/2008 | Shafer | G03F 7/70225 |
| | | | 359/727 |
| 2012/0092616 A1 | 4/2012 | Peyman | |
| 2015/0062531 A1 | 3/2015 | Buckland | |

FOREIGN PATENT DOCUMENTS

| | | | |
|---|---|---|---|
| JP | A H07-056090 A | 3/1995 | |
| JP | A 2005-037896 A | 2/2005 | |
| JP | B 5649324 B2 | 1/2015 | |
| JP | B 5806257 B2 | 11/2015 | |
| WO | WO-2008037346 A1 * | 4/2008 | ......... G02B 21/0032 |
| WO | WO-2010/044942 A1 | 4/2010 | |
| WO | WO-2010/125394 A1 | 11/2010 | |

OTHER PUBLICATIONS

Extended European Search Report issued in corresponding European Patent Application No. 17848772.4 dated Apr. 9, 2020.
International Search Report and Written Opinion issued in International Application No. PCT/JP2017/031999 dated Dec. 26, 2017.
"Galvanometer Scanners with Unmatched Flexibility, Speed, Accuracy, and Reliability", Cambridge Technology, A Novanta Company, 2019 (copyright) (https://www.cambridgetechnology.com/products/galvanometer-scanner).

* cited by examiner

Fig. 4A
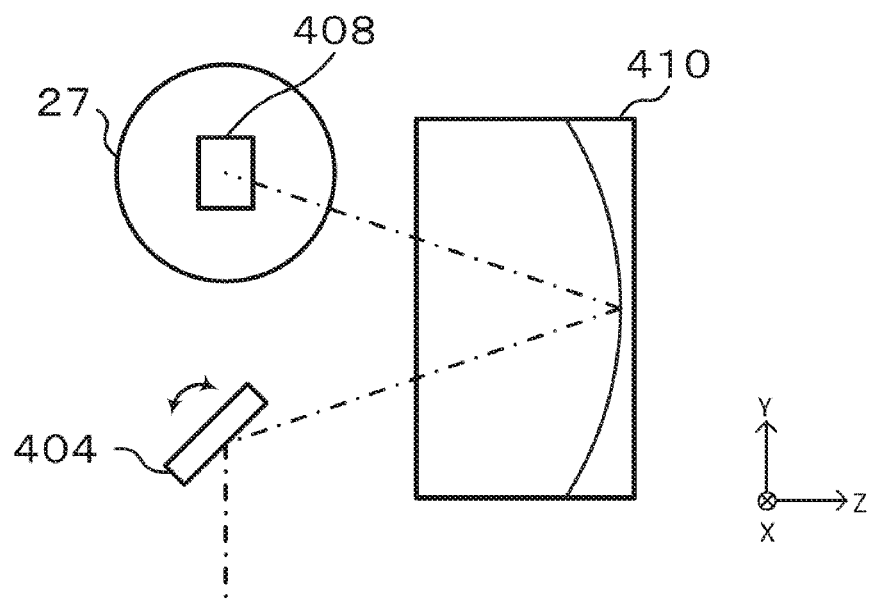
[Fig. 4B]
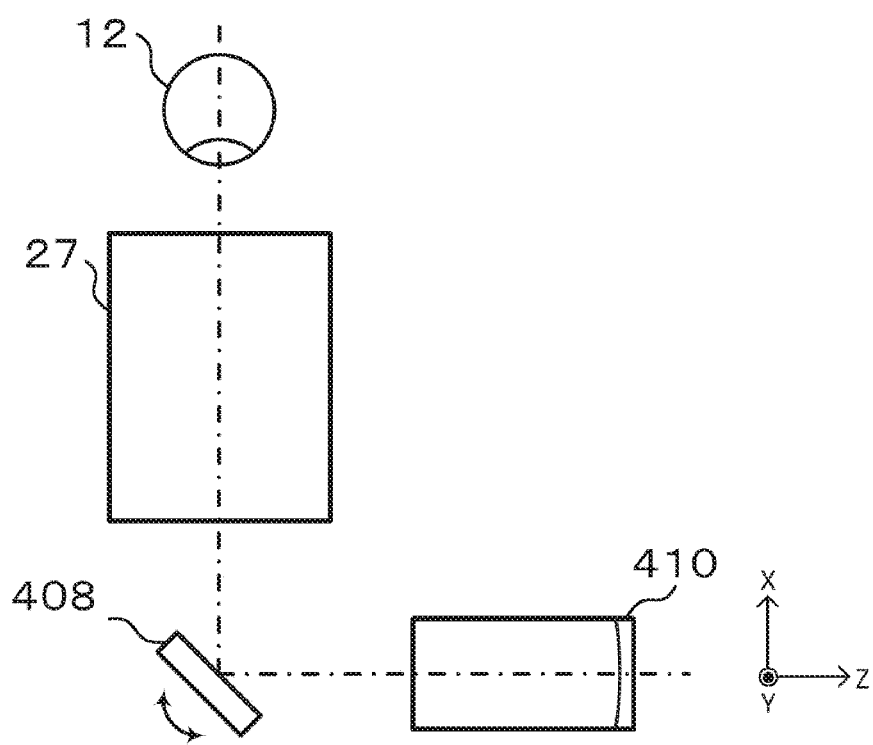

[Fig. 5A]
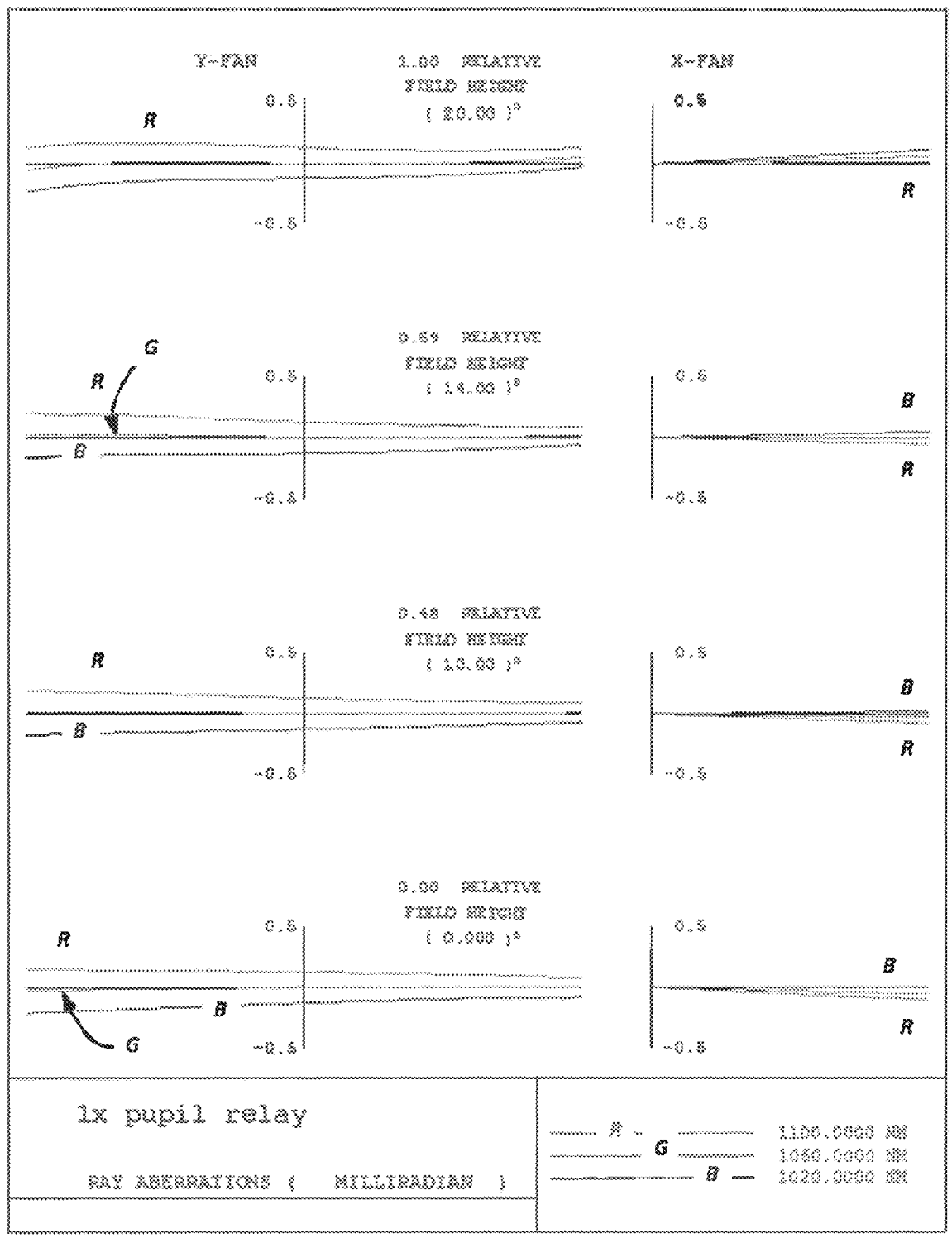

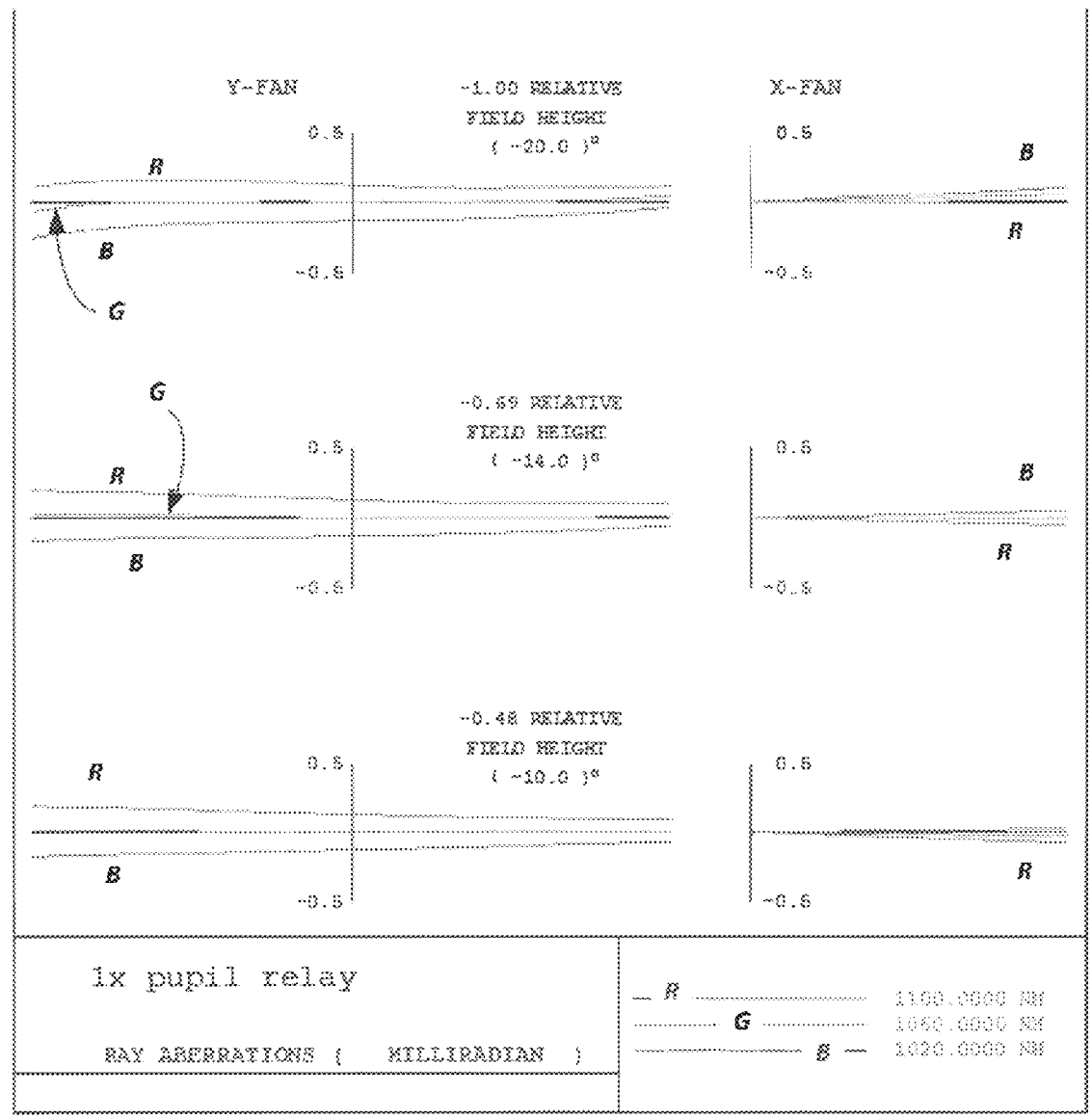
[Fig. 5B]

[Fig. 6A]
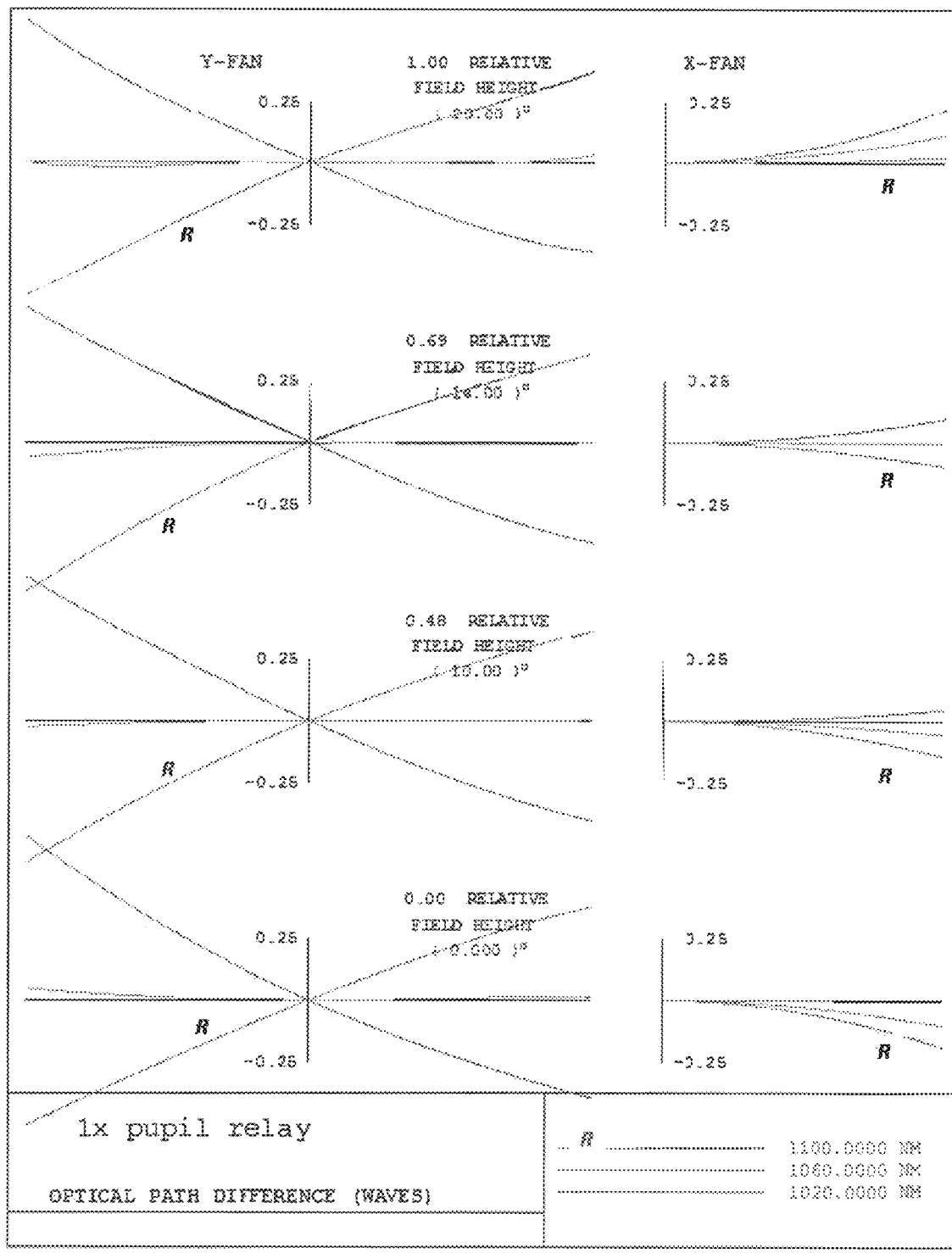

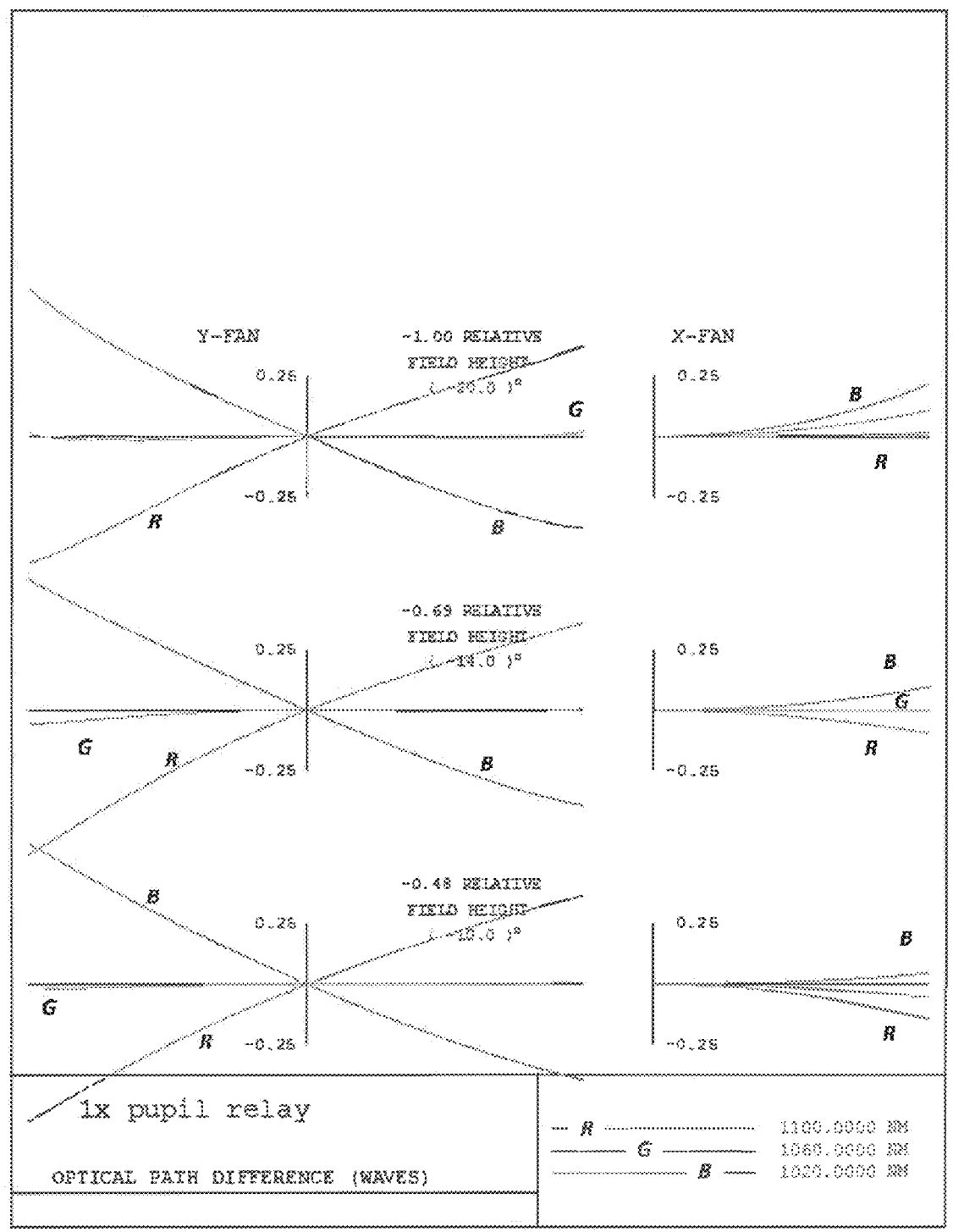

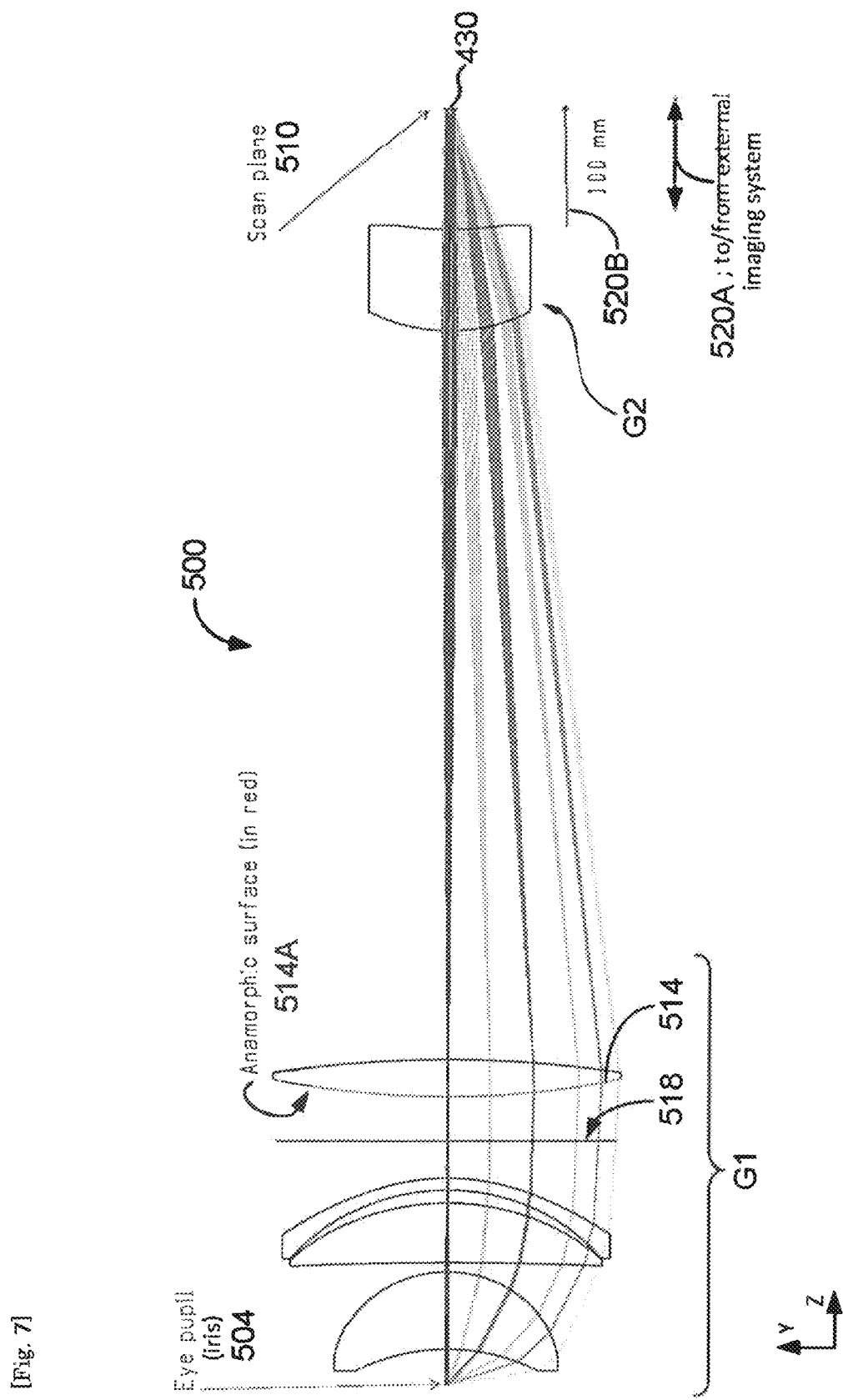
[Fig. 7]

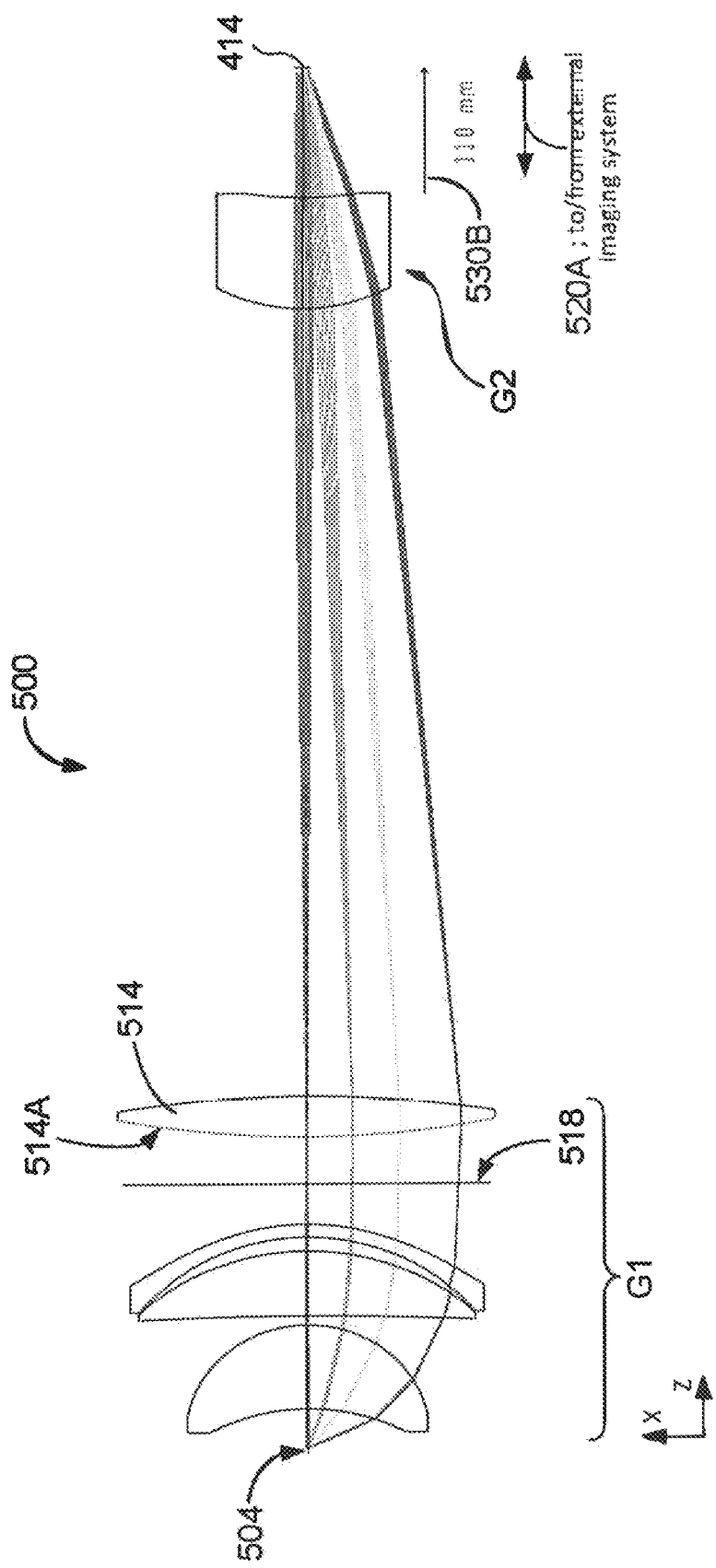
[Fig. 8]

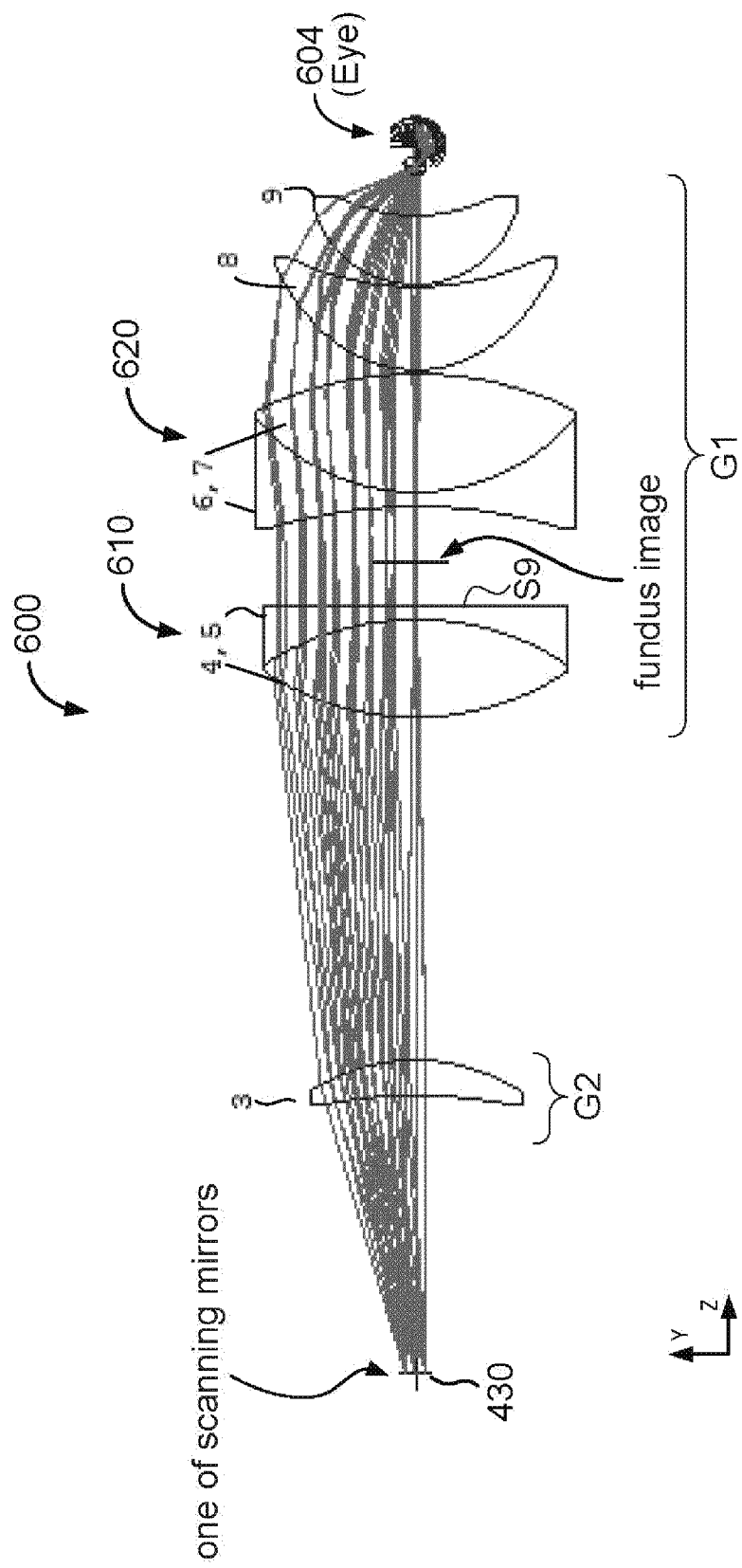

CATADIOPTRIC UNIT-MAGNIFICATION AFOCAL PUPIL RELAY AND OPTICAL IMAGING SYSTEM EMPLOYING THE SAME

TECHNICAL FIELD

The present invention is a continuation of PCT Application No. PCT/JP2017/031999, filed Sep. 5, 2017, which technically relates to U.S. Provisional Patent Application No. 62/383,722 filed on Sep. 6, 2016, U.S. Provisional Patent Application No. 62/480,886 filed on Apr. 3, 2017, US Provisional Patent Application No. 62/383,745 filed on Sep. 6, 2016, and U.S. Provisional Patent Application No. 62/475,069 filed on Mar. 22, 2017. The disclosures of these provisional applications are incorporated herein by reference.

The present invention relates generally to a methodology of wide-angle optical imaging of a retina and, more specifically, to a catadioptric afocal pupil relay system and an anamorphic afocal optical pupil relay system.

BACKGROUND ART

Various optical imaging systems continue to employ scanning reflectors and are therefore in need of imaging of one of such scanning reflector onto another (as part of the imaging process through the optical system).

In principle, a conventional unit-magnification afocal relay (configured as a telescope) can image one of the scanning mirrors on to the other. However, in order to achieve favorable image quality at finite light beam apertures, the refracting lenses used in such a telescopic arrangement typically end up being rather long (which complicates their use) and intricate from the design point of view. In commercial x-y galvanometer scanning mirrors (an example of which is produced by Cambridge Technology, Inc.), for instance, there exists an operationally-necessary physical separation between the mirrors scanning the light beam in x- and y-directions (referred to as x- and y-scanning mirrors, respectively) which prevents the mirrors from being optically conjugate with each other—they are not, in effect, optically superimposed on each other. If these mirrors, which are spatially-separated from one another, are optically relayed or imaged by means of an isotropic afocal telescope, the images of these mirrors still remain unconjugated with each other.

Such system configuration implies that the optical beams scanning in x- and y-directions at the output of the system (beams scanning horizontally and vertically), as viewed from the image plane, do not appear to originate from both of the scanning mirrors at the same time. Stated differently, at least one of such scanning output beams ends up being displaced relative to the ideal pupil position. This displacement presents a practical problem for an ultra-wide-angle system that has to effectuate optical imaging of an object through a small diameter pupil such as that of the undilated human eye (iris)—the scanning beams "wander" in the pupil across the field of view, which can cause vignetting at wide field angles, or loss of imaging of some parts of the field of view.

Furthermore, scan angles of a typical galvanometer mirror are usually limited to a full-angle of about 40 degrees (+1/−20 degrees). To increase the scan angle to that of the field of view (FOV) of the eye, a magnifying telescope may be required.

Related art such as U.S. Pat. Nos. 5,815,242 and 7,959,290 disclose the use of an ellipsoidal mirror (instead of an afocal relay) to image one scanning mirror onto the other. However, as is known to those skilled in the art, such an ellipsoidal mirror introduces significant aberrations at finite apertures. These aberrations either have to be compensated for by means of complicated dynamic optical elements during the scan, as described in U.S. Pat. No. 5,815,242, or to be tolerated by keeping the aperture as small as possible (which, in turn, inevitably reduces diffraction-limited resolution). The additional practical disadvantage of this approach stems from the difficulty of manufacturing an ellipsoidal mirror to the required accuracy for precision scanning.

Therefore, there remains a need to overcome the deficiencies of current state-of-the-art methodologies of producing an image on the retina when imaging involves the use of x- and y-beam-scanning systems.

SUMMARY OF INVENTION

A first aspect of the present disclosure includes first and second scanning reflectors, the first scanning reflector being configured to scan a beam of light incident thereon in a first plane, the second scanning reflector being configured to scan a beam of light incident thereon in a second plane, and the first and second planes being transverse to one another; and a catadioptric afocal relay system disposed along the optical axis in optical communication with, and between, the first and second scanning reflectors, the catadioptric afocal relay system being configured to image one of the first or second scanning reflectors onto another of the first or second scanning reflectors, in light propagating along the optical axis, with a unit magnification, and the catadioptric afocal relay system including only one reflector.

BRIEF DESCRIPTION OF DRAWINGS

The invention will be more fully understood by referring to the following detailed description of specific embodiments in conjunction with the not-to scale drawings.

FIG. 4A is a diagram showing an example of a side view of X-Y scanner unit 23.

FIG. 4B is a diagram showing an example of a front view of X-Y scanner unit 23.

FIG. 5A shows a multiplicity of plots representing ray aberrations for different field heights.

FIG. 5B shows a multiplicity of plots representing ray aberrations for different field heights.

FIG. 6A presents a plurality of plots illustrating the optical path difference in the embodiment of the invention for light at different wavelengths, for the same relative field height values as those of FIGS. 5A and 5B.

FIG. 6B presents a plurality of plots illustrating the optical path difference in the embodiment of the invention for light at different wavelengths, for the same relative field height values as those of FIGS. 5A and 5B.

FIG. 7 is a cross-sectional view of a second embodiment of the invention in one of the sagittal and meridional planes.

FIG. 8 is a cross-sectional view of the second embodiment of the invention in another of the sagittal and meridional planes.

FIG. 10 is a cross-sectional view of another embodiment of the invention.

Figure 1:
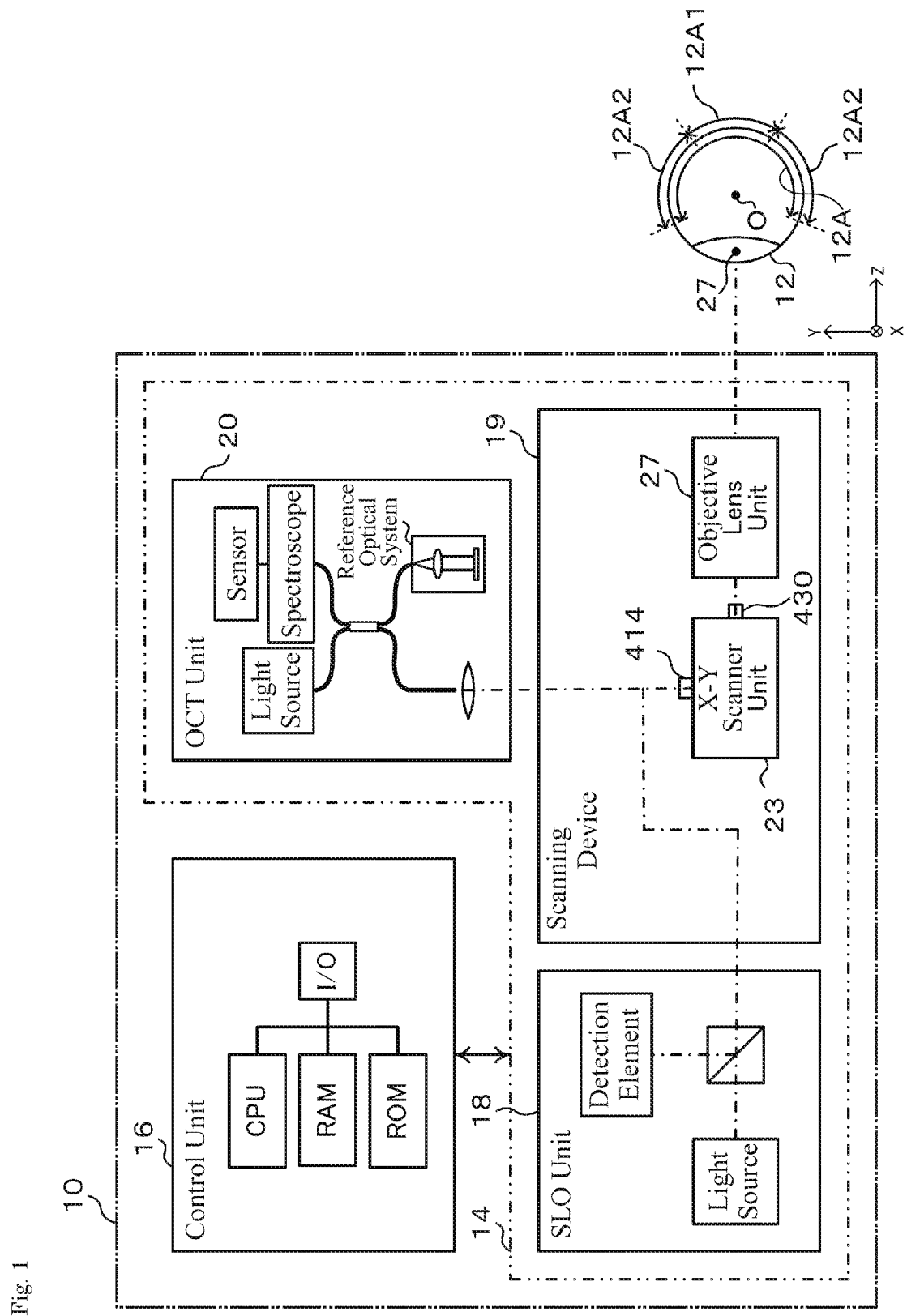
FIG. 1 is a diagram showing an example of the configuration of ophthalmic imaging device 10 according to the present embodiment.

Generally, the sizes and relative scales of elements in the drawings may be set to be different from actual ones to appropriately facilitate simplicity, clarity, and understanding of the drawings. For the same reason, not all elements present in one drawing may necessarily be shown in another.

DESCRIPTION OF EMBODIMENTS

FIG. 1 shows an example of the configuration of ophthalmic imaging device 10 according to the present embodiment.

As shown in FIG. 1, ophthalmic imaging device 10 includes device main body 14 that images the fundus of the subject eye, and control device 16. In the following explanation, "imaging" refers to the acquisition of an image showing the imaging target by means of a user using ophthalmic imaging device 10, which is also referred to as "image capture". Device main body 14 operates under the control of control device 16. Device main body 14 includes SLO unit 18, scanning device 19, and OCT unit 20.

In the following explanation, in a case in which ophthalmic imaging device 10 is installed on a horizontal surface, the horizontal direction is referred to as the "X direction", a vertical direction relative to the horizontal direction is referred to as the "Y direction", and a direction facing the fundus from the anterior ocular segment of subject eye 12 via eyeball center O is referred to as the "Z direction". Accordingly, the "X direction" is perpendicular to both of the Y direction and the Z direction.

Ophthalmic imaging device 10 according to the present embodiment has two functions that exemplify the main functions that can be realized by ophthalmic imaging device 10. The first function is a function whereby ophthalmic imaging device 10 is operated as a Scanning Laser Ophthalmoscope (SLO), and imaging is performed by the SLO (hereinafter, referred to as an "SLO imaging function"). The second function is a function whereby ophthalmic imaging device 10 is operated according to Optical Coherence Tomography (OCT), and imaging is performed by OCT (hereinafter, referred to as an "OCT imaging function").

The SLO imaging function is realized, from among the components of ophthalmic imaging device 10, by control device 16, SLO unit 18, and scanning device 19, which includes X-Y scanner unit 23 and objective lens unit 27. SLO unit 18 includes, for example, a light source and a detection element, and is capable of capturing an image of the fundus of subject eye 12. That is, by operating ophthalmic imaging device 10 according to the SLO imaging function, an image of the fundus of subject eye 12 (for example, imageable region 12A) is captured as the imaging target. Specifically, light from SLO unit 18 (hereinafter, referred to as "SLO light") is scanned by scanning device 19 with respect to imageable region 12A via the pupil of subject eye 12, by X-Y scanner unit 23 in the Y direction (vertical direction) and in the X direction (horizontal direction), and an image is acquired at SLO unit 18 from the reflected light. Detailed explanation is omitted as the SLO imaging function is a well-known function.

The OCT imaging function is realized by control device 16, OCT unit 20, and scanning device 19, which includes X-Y scanner unit 23 and objective lens unit 27. OCT unit 20 includes, for example, a light source, a spectroscope, a sensor and a reference optical system, and is capable of capturing images of plural tomographic regions in a film thickness direction of the fundus. That is, by operating ophthalmic imaging device 10 according to the OCT imaging function, images are captured of tomographic regions, which are regions in a film thickness direction of the fundus (for example, imageable region 12A). Specifically, light from OCT unit 20 (hereinafter, referred to as "measurement light") is scanned by scanning device 19 with respect to imageable region 12A via the pupil of subject eye 12, by X-Y scanner unit 23 in the Y direction (vertical direction) and in the X direction (horizontal direction), and interference light is produced using reflected light of the measurement light and reference light. OCT unit 20 detects each spectral component of the interference light and, using the detection results, control device 16 acquires a physical quantity (for example, a tomographic image) showing the tomographic regions. Detailed explanation is omitted as the OCT imaging function is a well-known function.

In the following explanation, since the SLO light and the measurement light are both light that is scanned two-dimensionally in the X direction and the Y direction, the SLO light and the measurement light are referred to together as "scanning light" when there is no need to provide explanation that distinguishes between the SLO light and the measurement light.

The operational problem(s) caused by the use of an optical imaging system that employs two reflectors that are axially-separated from one another (each of which is configured to contribute to the process of imaging of the object, but in different planes that are transverse to each other) is solved by complementing the optical imaging system with a magnifying anamorphic afocal optical relay system configured to image both of these reflectors onto a single plane of the optical pupil with a substantially high angular magnification. In a case in which each of the two reflectors, which are axially-separated from one another, is configured to scan, within a certain limited scan angle, the beam of light incident thereon in a respectively corresponding plane, the use of such a magnifying anamorphic afocal optical pupil relay also overcomes the numerical limitation of the scan angles by increasing the scan angles of the resulting combined optical imaging system.

One solution stems from the realization that the catadioptric afocal relay may be judiciously configured to avoid the shortcomings of the existing solutions—both those utilizing the ellipsoidal re-imaging optical elements and those utilizing purely dioptric reimaging elements.

X-Y scanner unit 23 is explained in detail.

Figure 2:
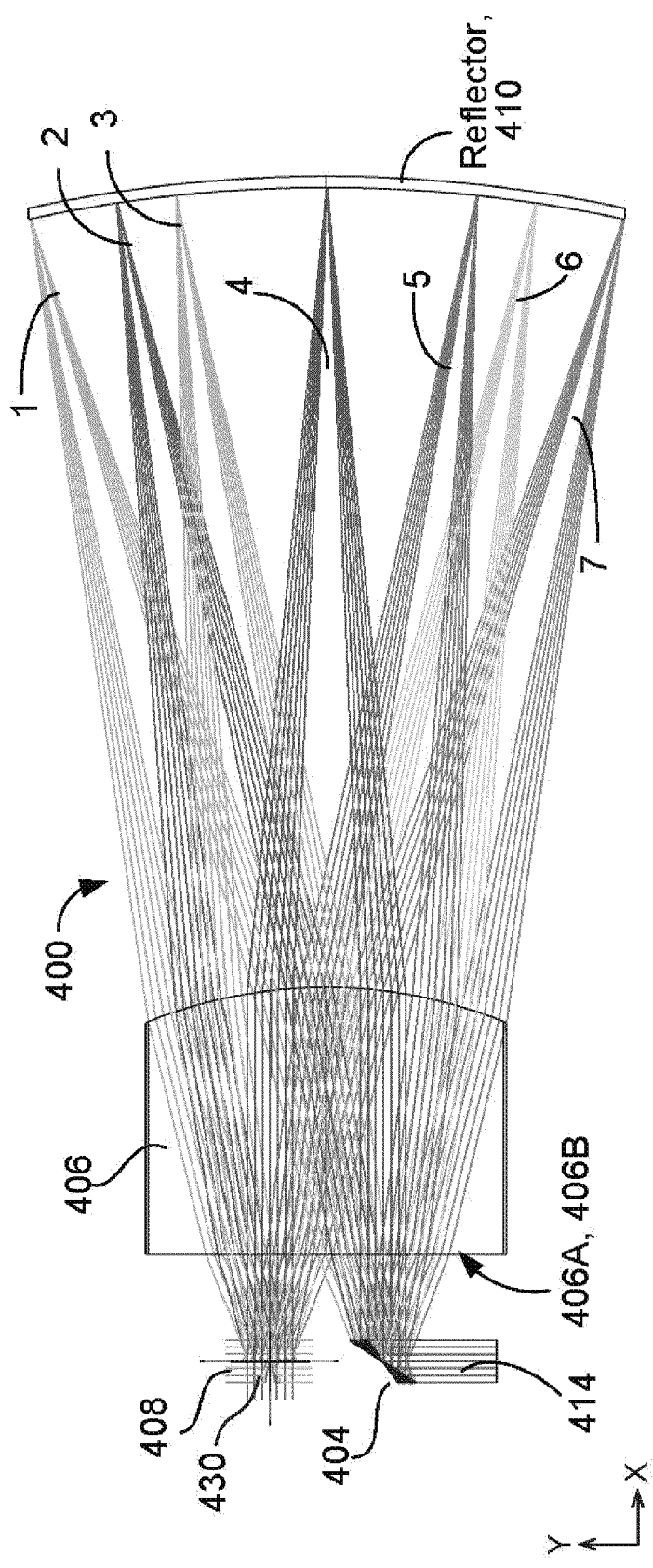
FIG. 2 illustrates a first embodiment of the catadioptric afocal relay of unit-magnification relay configured for imaging of one scanning mirror of the OCT system onto another scanning mirror of such a system, in cross-sectional view.

FIG. 2 shows a cross-section through a relay 400 that is configured as a Dyson-type relay to image the mirror 404 (which is disposed to scan the light beam, incident onto this mirror, in one plane; for example, the yz-plane) onto the mirror 408 (configured to scan the light beam, incident onto this mirror, in another plane that is transverse to the plane of scanning of the mirror 404; for example the xz-plane). The relay 400 may be a part of another, selected, optical system. The propagation of light through the relay 400 includes the propagation of light reflected off of the mirror 404 through the first element of the relay (shown as 406) towards the reflector 410 and then back to and through the third element of the relay (the role of which is played by the same element 406) and towards the mirror 408. The term transverse, unless specifically defined herein otherwise, is used to identify a situation in which one of the elements referred to as being transverse with respect to another is lying or extending across the other element or in a cross direction, and is not parallel to the other element.

Figure 3:
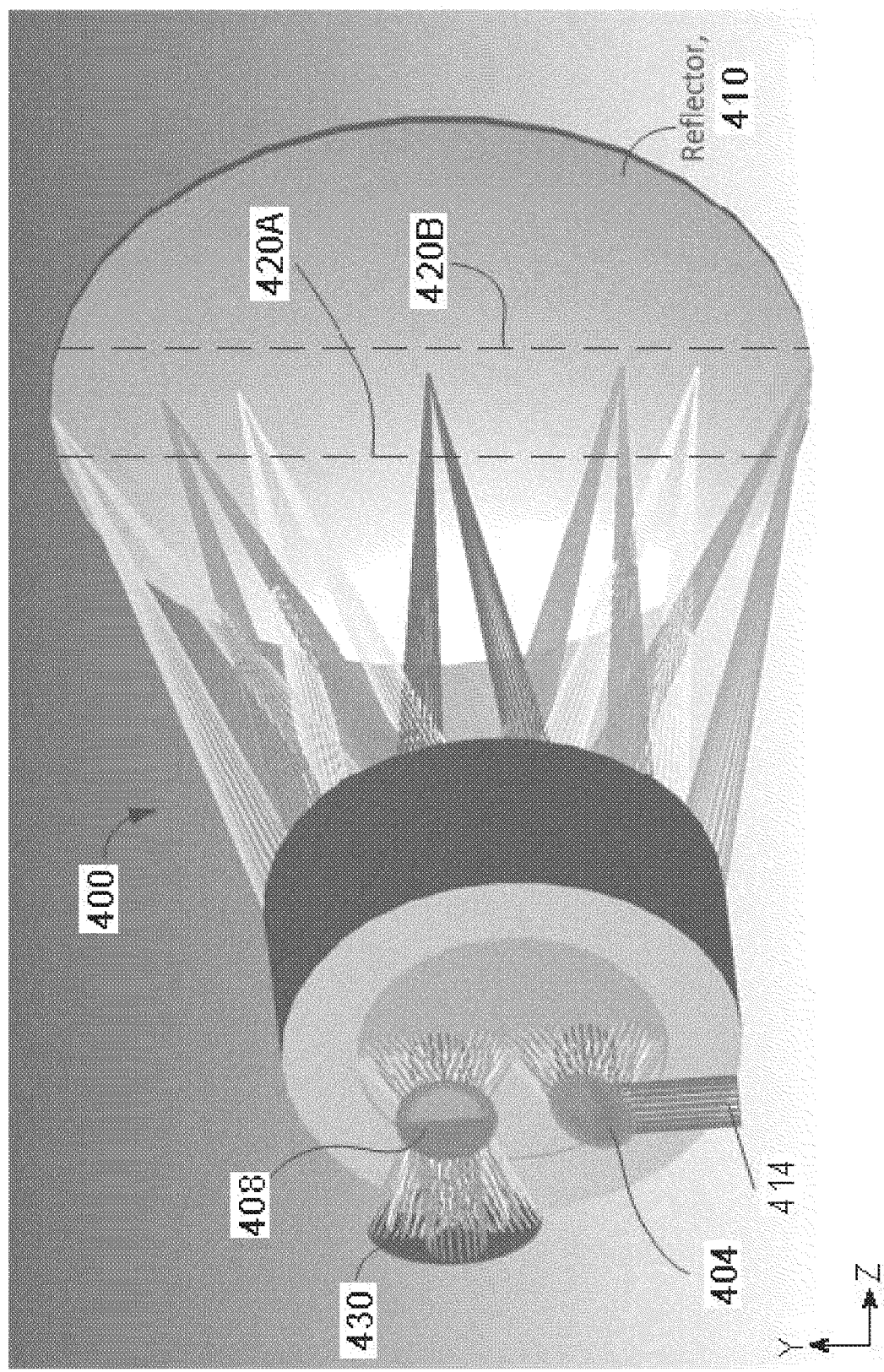
FIG. 3 illustrates a first embodiment of the catadioptric afocal relay of unit-magnification relay configured for imaging of one scanning mirror of the OCT system onto another scanning mirror of such a system, in perspective view.

Notably, and in stark contradistinction with conventional Dyson systems employed in the related art in a finite-conjugate imaging system, in the Dyson-type system of the present invention the roles of pupil and image are reversed and the relay 400 is configured as a unit magnification afocal relay. Positions across a reflector 410, indicated with numerals "1", "2", "3", and so on, show the locations of the input light beam 414 that has been y-scanned by the reflector 404 (and which enters the optical imaging system and strikes vertically-scanning mirror 404 from the bottom as shown) at the surface of the reflector 410. FIG. 3 shows a perspective view of the embodiment 400 of FIG. 2, where the light beam 414 enters the system 400 from the bottom, and the beam 430, which has been scanned in two transverse planes by the mirrors 404, 408, appears to emerge from the top scan mirror. The reflector 410 (in a specific implementation, a spherical reflector) can have a circular aperture (as viewed along its optical axis). Alternatively, the reflector 410 can be truncated to a narrow rectangular ("strip") aperture, which would be all that is used in practice in one embodiment during the scanning of the input beam 414. The alternative embodiment of the relay system of the invention in which the area and clear aperture of the reflector is reduced to that of the reflecting "strip" is shown in the same FIG. 3; here, the boundaries of the alternative implementation of the strip-shaped reflector are indicated with the lines 420A, 420B. As shown in FIG. 3, the effective reflection region between lines 420A and 420B is elongated along the scanning direction by the vertically scanning mirror 404. Because the embodiment of the system operates at unit magnification, the optical distortion is infinitesimal, if present at all.

Further, FIG. 4A shows X-Y scanner unit 23, which relates to a light beam scanned by Y-scanning mirror 404, and FIG. 4B shows X-Y scanner unit 23, which relates to a lightbeam scanned by X-scanning mirror 408. Reflector 410 includes a reflector that reflects a width region corresponding to the beam diameter of a light beam irradiated along a scanning path in X-Y scanner unit 23. Further, the width of the effective reflection region at the reflector surface can be any integer multiple of the scanning beam diameter (for example, 2 mm), preferably a multiple of approximately 2 to 10 is effective, and 10 mm is preferable in terms of practical application. In order to maintain the surface accuracy of the reflective surface and support the reflector within the device, the shape of the reflector itself may be circular, a rectangle inscribed within the circle, or an ellipse, and the shape of the reflective region may be a narrow rectangle as described above.

Since the x-scan mirror 408 is optically conjugate (with 1× magnification via the relay 400) with the y-scan mirror 404, these scanning mirrors are re-imaged exactly and precisely to another, auxiliary, pupil position by means of any isotropic afocal relay or F-theta lens system. Two points are considered to be optically-conjugate with one another when the image of the object placed at one of the points is located at another of the points. This provides a practical solution to operational problems persistently experienced by the users of ultra-wide-angle scanning systems that have to form optical images through a small-diameter pupil, such as that of an undilated eye. Advantages of the proposed configuration include: (i) well-corrected aperture aberrations; (ii) lack of angular distortion; and (iii) simple and compact design due to the presence of only spherical surfaces, and the operational limitation of this design comes from limited angular magnification, which necessarily limits the linear and, therefore, solid or spatial, angle(s) over which the retinal surface can be scanned with the use of an optical system complemented with such a catadioptric afocal relay unit.

Notably, the embodiment of the system contains only one, single, reflector (the reflector 410).

TABLE 1

| ELEMENT NUMBER | RADIUS OF CURVATURE FRONT | RADIUS OF CURVATURE BACK | THICKNESS | APERTURE DIAMETER FRONT | APERTURE DIAMETER BACK | MATERIAL Nd | MATERIAL Vd |
|---|---|---|---|---|---|---|---|
| OBJECT | | INF | INFINITY | | | | |
| | | | APERTURE STOP 20.0000 | 8.0000 | | | |
| | | DECENTER(1) | | | | | |
| | | | 0.0000 | 42.5588 | | | |
| 1 | A(1) | −97.6279 CX | 60.2353 | 43.0281 | 65.9373 | 1.51680 | 64.2 |
| | | | 145.4560 | | | | |
| 2 | | −235.3933 CC | −145.4560 | | 107.0744 | REFL | |
| 3 | −97.6279 CX | A(2) | −60.2353 | 65.7014 | 42.7238 | 1.51680 | 64.2 |
| | | | 0.0000 | | | | |
| | | DECENTER(2) | | | | | |
| | | | | | 22.2682 | | |
| | | IMAGE DISTANCE = −20.0000 | | | | | |
| IMAGE | | INF | | | 8.3205 | | |

NOTES:
Positive radius indicates the center of curvature is to the right.
Negative radius indicates the center of curvature is to the left.
Dimensions are given in millimeters.
Thickness is axial distance to next surface.
Image diameter shown above is a paraxial value, and is not a ray traced value.
Other glass suppliers can be used if their materials are functionally equivalent to the extent needed by the design; contact the designer for approval of substitutions.

TABLE 2

ASPHERIC CONSTANTS $$Z = \frac{(CURV)Y^2}{1 + (1 - (1+K)(CURV)^2 Y^2)^{1/2}} + (A)Y^4 + (B)Y^6 + (C)Y^8 + (D)Y^{10}$$

| ASPHERIC | CURV | K | A | B | C | D |
|---|---|---|---|---|---|---|
| A(1) | 0.308441E−02 | 0.00000000 | −2.78862E−07 | −2.02506E−10 | 2.17101E−13 | 0.00000E+00 |
| A(2) | 0.308441E−02 | 0.00000000 | −2.78862E−07 | −2.02506E−10 | 2.17101E−13 | 0.00000E+00 |

TABLE 3

DECENTERING CONSTANTS

| DECENTER | X | Y | Z | ALPHA | BETA | GAMMA |
|---|---|---|---|---|---|---|
| D(1) | 0.0000 | 10.0000 | 0.0000 | 0.0000 | 0.0000 | 0.0000 |
| D(2) | 0.0000 | 10.0000 | 0.0000 | 0.0000 | 0.0000 | 0.0000 |

A decenter defines a new coordinate system (displaced and/or rotated) in which subsequent surfaces are defined. Surfaces following a decenter are aligned on the local mechanical axis (z-axis) of the new coordinate system. The new mechanical axis remains in use until changed by another decenter. The order in which displacements and tilts are applied on a given surface is specified using different decenter types and these generate different new coordinate systems; those used here are explained below. Alpha, beta, and gamma are in degrees.

DECENTERING CONSTANT KEY:

| TYPE | TRAILING CODE | ORDER OF APPLICATION |
|---|---|---|
| DECENTER |  | DISPLACE (X, Y, Z) |
|  |  | TILT (ALPHA, BETA, GAMMA) |
|  |  | REFRACT AT SURFACE |
|  |  | THICKNESS TO NEXT SURFACE |

TABLE 3-continued

REFERENCE WAVELENGTH = 1060.0 NM
SPECTRAL REGION = 1020.0-1100.0 NM

This is a non-symmetric system. If elements with power are decentered or tilted, the first order properties as determined from the paraxial ray trace may be inaccurate.
INFINITE CONJUGATES
EFL = −31712.0399
BFL = 31691.3907
FFL = 31711.3907
F/NO = 3964.0050
IMAGE DIST = −20.0000
OAL = 20.0000
PARAXIAL
IMAGE HT = 11542.2386
SEMI-FIELD
ANGLE = 20.0000
ENTR PUPIL
DIAMETER = 8.0000
DISTANCE = 0.0000
EXIT PUPIL
DIAMETER = 8.0002
DISTANCE = −21.2984

NOTES:
FFL is measured from the first surface.
BFL is measured from the last surface.

TABLE 4

WAVEFRONT ANALYSIS

| X REL. FIELD | 0.00 | 0.00 | 0.00 | 0.00 | 0.00 |
|---|---|---|---|---|---|
|  | 0.00 | 0.00 |  |  |  |
| Y REL. FIELD | 0.00 | 0.48 | 0.69 | 1.00 | −0.48 |
|  | −0.69 | −1.00 |  |  |  |
| WEIGHTS | 1.00 | 1.00 | 1.00 | 1.00 | 1.00 |
|  | 1.00 | 1.00 |  |  |  |
| NUMBER OF RAYS | 316 | 308 | 304 | 292 | 312 |
|  | 304 | 292 |  |  |  |
| WAVELENGTHS | 1100.0 | 1060.0 | 1020.0 |  |  |
| WEIGHTS | 0 | 1 | 0 |  |  |

| FIELD | | | BEST INDIVIDUAL FOCUS | | | BEST COMPOSITE FOCUS | | |
|---|---|---|---|---|---|---|---|---|
| | | FOCUS | RMS | STREHL | FOCUS | RMS | STREHL |
| FRACT | DEG | SHIFT | (MR) | (DIO) | (WAVES) | SHIFT | (MR) | (DIO) | (WAVES) |
| X 0.00 | 0.00 | 0.000000 | 0.005002 | 0.0286 | 0.968 | 0.000000 | 0.000341 | 0.0304 | 0.964 |
| Y 0.00 | 0.00 | −0.004814 | | | | −0.004814 | | | |
| X 0.00 | 0.00 | 0.000000 | 0.004489 | 0.0093 | 0.997 | 0.000000 | 0.000341 | 0.0129 | 0.993 |
| Y 0.48 | 10.00 | 0.001470 | | | | 0.001470 | | | |
| X 0.00 | 0.00 | 0.000000 | 0.002532 | 0.0076 | 0.998 | 0.000000 | 0.000341 | 0.0089 | 0.997 |
| Y 0.69 | 14.00 | 0.005100 | | | | 0.005100 | | | |
| X 0.00 | 0.00 | 0.000000 | −0.009931 | 0.0237 | 0.978 | 0.000000 | 0.000341 | 0.0317 | 0.961 |
| Y 1.00 | 20.00 | 0.006161 | | | | 0.006160 | | | |
| X 0.00 | 0.00 | 0.000000 | 0.004489 | 0.0097 | 0.996 | 0.000000 | 0.000341 | 0.0132 | 0.993 |
| Y −0.48 | −10.00 | 0.001529 | | | | 0.001529 | | | |

TABLE 4-continued

| | | | | | | | | | |
|---|---|---|---|---|---|---|---|---|---|
| X | 0.00 | 0.00 | 0.000000 | 0.002383 | 0.0074 | 0.998 | 0.000000 | 0.000341 | 0.0086 | 0.997 |
| Y | −0.69 | −14.00 | 0.005452 | | | | 0.005452 | | | |
| X | 0.00 | 0.00 | 0.000000 | −0.009629 | 0.0235 | 0.979 | 0.000000 | 0.000341 | 0.0311 | 0.963 |
| Y | −1.00 | −20.00 | 0.004565 | | | | 0.004566 | | | |

COMPOSITE RMS FOR POSITION 1:0.02189
Units of RMS are waves at 1060.0 nm.

NOTE: Strehl is the intensity at the peak of the point image as a fraction of the peak of the aberration-free image with the same vignetting and obscuration. The approximation used here is generally valid for: RMS < 0.1.?

Referring again to FIG. 2, and in further reference to Table 1, optical elements interacting with light propagating through the relay 400 on its way from the reflector 404 to the reflector 408 and forming an image on the reflector 408 are sequentially tabulated and numbered as elements 1 through 3. The entrance surface of the relay (surface 40A of the lens 406)—which, at the same time, represents the exit surface (surface 406B) of the relay—is an aspheric surface, the parameters of which are summarized in Table 2. Table 3 discusses the decentering constants used in the design of the system 400.

Table 4 summarizes the results of the analysis of the wavefront of light propagating through the embodiment 400 in the spectral range from 1020 nm to 1100 nm, for several values of the field height (in the range from 20 degrees, considered to be a field height of 1, to −20 degrees, considered to be a field height of −1). It is readily observed that, with respect to the best individual focus, the Strehl ratio characterizing the imaging is higher than 0.96 anywhere across the field range both with respect to the best individual focus and with respect to the best composite focus. Accordingly, the operation of the embodiment of the invention in light at wavelengths within a spectral range from 1020 nm to 1100 nm is characterized by a first Strehl ratio at a central wavelength of the range (such as 1060 nm, for example) and a second Strehl ratio at any wavelength of said range, with both the first and second Strehl ratios exceeding 0.96.

FIGS. 5A and 5B complement the description of the design of the relay 400 by illustrating the values of ray aberrations, for each of the three chosen wavelengths within the spectral range considered for this design, at the same values of field heights as those summarized in Table 4. Characteristically, it will be appreciated by a skilled artisan that the absolute values of ray aberrations of the Y-fan of rays do not exceed about 0.25 milliradians for any field height, while the absolute values of ray aberrations of the X-fan of rays are substantially smaller and do not exceed approximately 0.1 milliradian. The optical path difference, illustrated for light at wavelengths of 1020 nm, 1060 nm, and 1100 nm through the relay 400, does not exceed about 0.5 waves for any field height (for the Y-fan of rays) and is smaller than 0.25 waves for the X-fan of rays.

The value of the optical path difference of about 0.25 waves, as is appreciated by a skilled artisan, is thought of as evidencing a substantially "diffraction-limited" system (which historically goes back to the Rayleigh criterion for defocus). Accordingly, in the present implementation, the imaging provided by the system is almost perfect in the X-fan or rays, but greater than 0.25 waves in the Y-fan. The residual chromatic aberrations can be corrected in/by an anisotropic relay lens to the eye, added as a follow-up to the embodiment of the invention. Alternatively, the residual chromatic aberrations may be considered operably acceptable in some cases. An embodiment of the invention can be used by itself, or be complemented with an isotropic relay.

Disclosed aspects, or portions of these aspects, may be combined in ways not listed above. Accordingly, the invention should not be viewed as being limited to the disclosed embodiment(s).

Second Embodiment

Next, a second embodiment is explained.

While advantages of the proposed configuration include: (i) well-corrected aperture aberrations; (ii) lack of angular distortion; and (iii) simple and compact design due to the presence of only one spherical mirror surface, the operational limitation of this design comes from limited angular magnification, which necessarily limits the linear and, therefore, solid or spatial, angle(s) over which the retinal surface can be scanned with the use of an optical system complemented with such a catadioptric afocal relay unit.

As mentioned above, catadioptric solutions to the construction of anamorphic afocal relays, while possessing some operational advantages, are limited in terms of angular magnification, and practical use may require yet another additional magnifying telescope.

Embodiments of the present invention, therefore, address dioptric solutions. FIG. 7 shows a diagram representing a yz-cross section through a dioptric afocal relay (telescope) 500. For convenience, rays are traced from the eye pupil 504 (entrance pupil, EP, of the eye) on the left of FIG. 7 to a plane 510 in which the scan mirror of the external optical imaging system is situated. The external optical imaging system contains two scanning mirrors as discussed above, and is not shown, for simplicity of illustration. In practice, the relay 500 is employed with such a system. The plane 510 is optically-conjugate with the eye pupil 504. The yz-plane in this case corresponds to the horizontal section, in which the human eye has a full-angle field of view of about 160 degrees (+/−80 dg.) (see, for example, "Field guide to visual and ophthalmic optics", by Jim Schwiegerling, SPIE Press, page 59). The afocal system reduces this field angle by a factor of 4× to about 40 degrees (+/−20 degrees) for the scanning mirror. In other words, as far as light propagating in the opposite direction (from the scanning mirror located in the plane 510 towards the EP 504) is concerned, the scan angle is magnified by 4× to match the angular value of the FOV of the eye in the yz-plane.

The field lens element 514 to the right of the intermediate image plane 518 of the system 500 has one optical surface 514A that is anamorphic; that is, it has a different radius of curvature in the yz- and xz-planes, causing, therefore, the lens element 514 to be an anamorphic lens element. The field lens element 514 images the eye pupil in the yz-plane to a plane that is located at about 100 mm from the last element of the telescope, on the right of FIG. 7, as schematically indicated by arrows 520A, 520B. This is where the horizontal scan mirror of the external optical imaging system (not shown) is located.

FIG. 8 shows the same system 500 in the cross-section produced by the xz-plane, which corresponds to the vertical section in which the field of view of the eye is smaller than that in the horizontal cross-section, or about 130 degrees (+/−65 degrees). In this cross-section, the anamorphic lens 514 with a single anamorphic lens surface 514A images the eye pupil 504 to another plane located at about 110 mm distance from the last element of the telescope on the right of FIG. 8 (as indicated with the arrows 520A, 530B). This is where the vertical scan mirror of the external optical imaging system is located, which is separated, in this example, by about 10 mm from the horizontal scan mirror as viewed along the optical axis of the external optical imaging system. The magnification of such imaging provided by the field lens 514 is, again, approximately 4×. Generally, according to the idea of the invention, the measures or coefficients of magnification provided by the field lens in the two transverse planes (in this example, in vertical and horizontal cross-sectional planes of the relay 500) are not required to be exactly the same, because in practice the values of scan angles of the external optical imaging system can be somewhat adjusted to match the exact magnification value.

As is well understood in the art, and unless expressly specified otherwise, the term "anamorphic" applied to the optical lens refers to, and defines, a lens that is configured to form a version of an image that is compressed (or, alternatively, expanded) along one of the dimensions with respect to another. Stated differently, and unless expressly defined otherwise herein, an optical system is referred to as anamorphic when it has, or provides for, different magnification in its meridional and sagittal sections or planes. The term "afocal" defines an optical element or system pertaining to or having no finite focal point.

In the present embodiment, as shown in FIGS. 7 and 8, relay system 500 is configured, in order from the side of eye pupil 504, by first lens group G1 having positive refractive power and second lens group G2 having positive refractive power and being disposed at a significant interval from first lens group G1. Further, first lens group G1 has a positive meniscus lens having a concave surface facing the side of the eye, a positive lens having a surface with higher curvature facing the opposite side from the eye, a negative meniscus lens having a convex surface facing the opposite side from the eye, and the biconvex lens 514 discussed above that substantially functions as a field lens. Further, second lens group G2 is configured by a positive meniscus lens having a convex surface facing the side of the eye, which is disposed near conjugate points 414 and 430 of the eye pupil 504. Eye fundus image 518 is formed, in first lens group G1, between the positive lens functioning as a field of view lens, and the negative meniscus lens.

Figure 9:
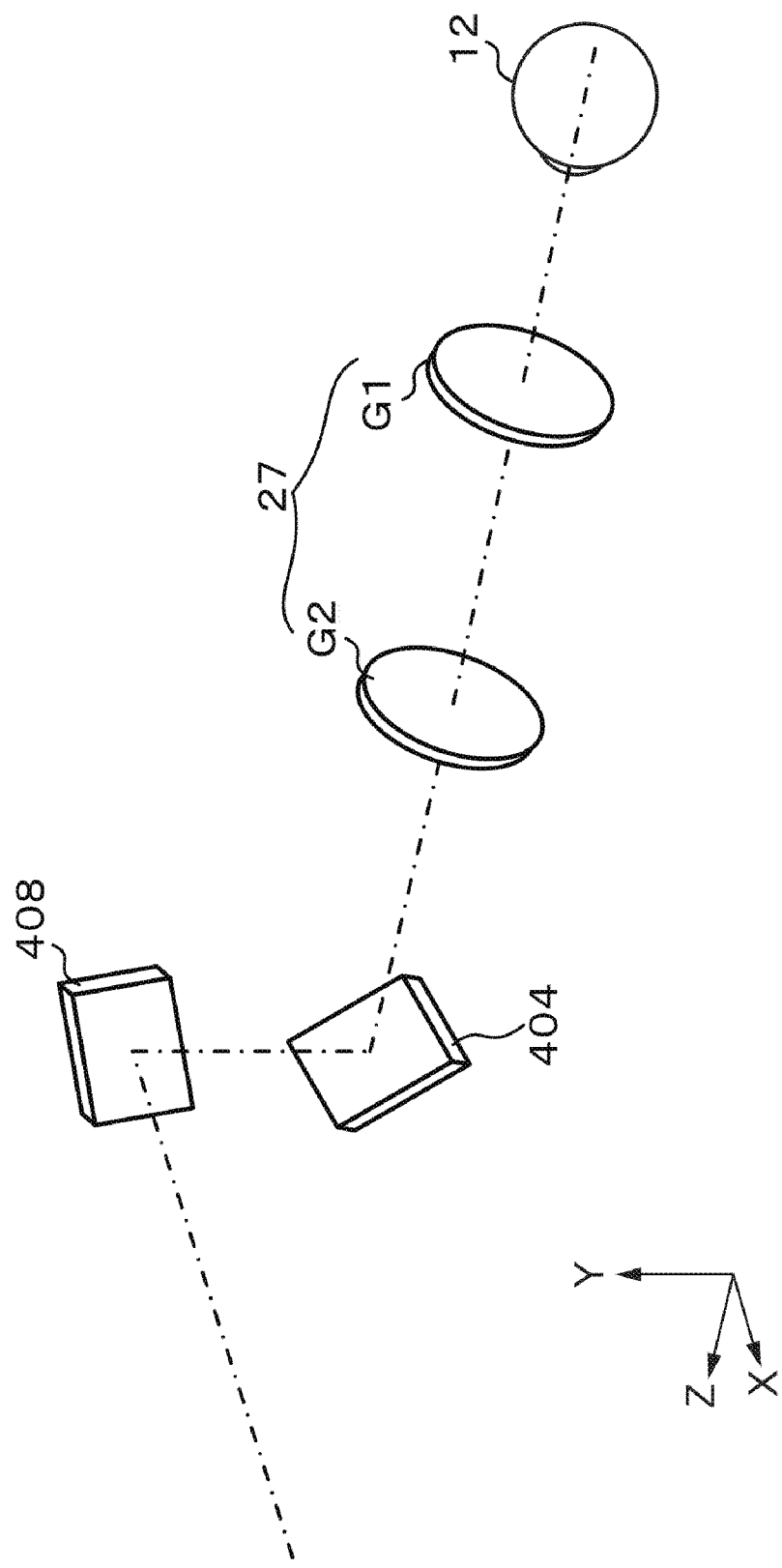
FIG. 9 is a perspective view showing an example of a front view of X-Y scanner unit 23.

FIG. 9 exemplifies a schematic diagram of X-Y scanner unit 23 and objective lens unit 27. In FIG. 9, objective lens unit 27 is configured by first lens group G1 and second lens group G2, which correspond to first lens group G1 and second lens group G2 in FIGS. 7 and 8 described above. That is, objective lens unit 27 is an anamorphic afocal optical pupil relay system as shown in FIGS. 7 and 8, and forms two conjugate points of the pupil of subject eye 12 at the respective positions of Y-scanning mirror 404 and X-scanning mirror 408, which are disposed at a remove therefrom. By this configuration, a laser beam from a light source not shown in the drawing is two-dimensionally scanned by X-scanning mirror 408 and Y-scanning mirror 404 at predetermined angles and guided to subject eye 12 through objective lens unit 27. By this anamorphic afocal optical pupil relay system, the center point of scanning at predetermined angles by X-scanning mirror 408 and Y-scanning mirror 404, which are disposed at positions removed from each other, is transferred to an identical point at the pupil surface of eye 12, and the laser beam is two-dimensionally scanned at the fundus of eye 12.

The dioptric afocal relay system shown in FIG. 7 and FIG. 8 functions as the objective lens unit 27 in FIG. 1 and forms an image of the retina of the eye in combination with the X-Y scanner unit 23 through the SLO unit 18 and/or OCT unit 20. As shown in FIG. 7, FIG. 8 and FIG. 9, the first scanning reflector 404 scans, in operation, a beam of light incident thereon in a first plane (Y-Z plane), and the second scanning reflector 408 scans a beam of light incident thereon in a second plane (X-Z plane). The first and second planes are orthogonally transverse to one another; and the first scanning reflector 404 and the second scanning reflector 408 are axially separated from one another along the optical axis of the optical system. The afocal optical relay system 500 has an anamorphic surface 514A as an anamorphic element and forms a first pupil image of the eye onto the first scanning reflector 404 in the first plane and forms a second pupil image of the eye onto the second scanning reflector 408 in the second plane. The magnification of the first pupil image in the first plane and the magnification of the second pupil image in the second plane are both greater than unity. This means that the maximum angle of the light on the eye side (θ2) is larger than the maximum angle of the scanning mirror side (θ1); that is, the ratio (θ2)/(θ1) is greater than 1. Then, the scanning angles by both the first and second scanning reflectors 404 and 408 are enlarged at the position of the pupil of the eye. By the Lagrange Invariant, the diameter of the light beam entering the eye is smaller than the diameter of the beam at the scanning mirrors by the same ratio as the angular magnification. Such configuration of the optical system is greatly advantageous for the ultra-wide field view in OCT as well as SLO.

FIG. 10, similarly to FIGS. 7 and 8, shows a cross-sectional view of another embodiment of an anamorphic afocal optical pupil relay system that functions as objective lens unit 27. In this relay system, too, the conjugate point of the eye pupil is formed at positions removed in the x and y directions; however, since the shapes of the lenses other than the anamorphic lens are identical, a cross-sectional view perpendicular to this drawing is omitted.

FIG. 10 schematically illustrates a related embodiment 600 of the invention, specifically configured to provide for reduced lateral color aberration over a 1.0 to 1.1 micron wavelength band (which may be of importance for operation of an OCT system). In this diagram, and for the purposes of characterizing the quality of optical imaging, the eye 604 is schematically represented with its Navarro model. (The Navarro eye model is described in J Opt Soc Am A., 1985 Aug; 2(8): 1273-81: "Accommodation-dependent model of the human eye with aspherics", Navarro R., Santamaria J., Bescos J.)

Here, in comparison with the embodiment 500, cemented doublets 610, 620 are immediately adjacent to one another along the optical axis and are introduced to provide a longer eye relief distance (increased to about 17 mm or larger, as compared to the typical 15 mm relief of devices of the related art). The increased eye relief, in turn, allows for advantageous increase of the diameters of the eyepiece-lenses (elements 6, 7, 8, and 9). One of the doublets 610, 620 (specifically, the doublet 610) is configured as a field lens that, in a specific case, can include an anamorphic aspheric surface (for example, surface S9) to image separated X, Y scanning mirrors onto the eye pupil (as discussed in reference to FIGS. 7 and 8 above).

The specific lens configuration of the embodiment shown in FIG. 10 is explained. Similarly to the lens configuration shown in FIGS. 7 and 8, basically, the configuration has first lens group G1 having positive refractive power disposed at the side of eye 604 and second lens group G2 having positive refractive power disposed at the side of the conjugate point of eye 604. First lens group G1 includes, in order from the side of eye 604, positive meniscus lens 9 having a concave surface facing the side of the eye, positive meniscus lens 8 also having a concave surface facing the side of the eye, doublet lens 620, described above, formed by joining biconvex lens 7 and biconcave lens 6, and doublet lens 610, described above, which substantially functions as a field lens, having positive refractive power, and is formed by joining negative lens 5, having a surface with higher curvature facing the opposite side from the eye, and biconvex lens 4. Further, second lens group G2, which is disposed at a significant distance therefrom and near the conjugate position of the eye pupil, is configured by positive meniscus lens 3 having a convex surface facing the side of the eye. The eye fundus image is formed between the two doublet lenses 610, 620.

It is appreciated, therefore, that the embodiments of the anamorphic afocal pupil relay, when used in conjunction with an external optical system having two scanning reflectors (referred to as x- and y-scan mirrors, each of which is configured to scan a beam of light, incident thereon, in a plane that is transverse to the plane in which another reflector scans the beam of light), provides a remarkable operational advantage over the known solutions of the related art. Specifically, in such a situation, both x-scan mirror and y-scan mirror are re-imaged simultaneously and precisely to the same location, in which another optical pupil can be placed. This advantage is important for ultra-wide-angle scanning systems that have to image through a small pupil, such as that of an undilated eye. In the proposed solution, aperture aberrations are well corrected. The use of the proposed solution does not require any manufacture of complicated ellipsoidal mirrors for use in the external optical imaging system that otherwise, according to the related art, are often used in an attempt to achieve the same results in re-imaging of the two scan mirrors to the same location. The proposed solution can find its use in, for example, scanning laser ophthalmoscopes and/or retinal OCT (Optical Coherence Tomography) systems.

Disclosed aspects, or portions of these aspects, may be combined in ways not listed above. Accordingly, the invention should not be viewed as being limited to the disclosed embodiment(s).

REFERENCE SIGNS LISTS

10 Ophthalmic imaging device
12 Subject eye
16 Control device
18 SLO unit
20 OCT unit
23 X-Y scanner unit
27 Objective lens unit
404 Y-scanning mirror
408 X-scanning mirror

The invention claimed is:

1. An optical system configured for retinal imaging, the optical system having an optical axis and comprising:
    first and second scanners, the first scanner being configured to scan a beam of light incident thereon in a first plane, the second scanner being configured to scan a beam of light incident thereon in a second plane, and the first and second planes being orthogonal to one another; and
    a catadioptric afocal relay system disposed along the optical axis between the first and second scanners and configured to image one of the first or second scanners onto another of the first or second scanners, in light propagating along the optical axis, with a unit magnification,
wherein:
said catadioptric afocal relay system including a concave reflector and a positive lens spatially disposed between the two scanners and the concave reflector, the concave reflector reflecting a scanned light beam from said one of the first or second scanners through the positive lens and guiding the light beam toward said other of the first or second scanners again through the positive lens, and the concave reflector having an effective reflective region with a width that corresponds to the beam diameter of a light beam irradiated along a scanning path of the one of the first or second scanners, and with a length direction of said effective reflective region corresponding to the scanning direction of the first scanner or the second scanner.

2. The optical system according to claim 1, wherein said width of said effective reflective region at said reflective surface of said concave reflector is from two times to ten times said beam diameter.

3. An ophthalmic imaging device, comprising:
    the optical system according to claim 1; and
    an imaging unit configured to image an eye fundus using the optical system.

4. The ophthalmic imaging device according to claim 3, wherein the imaging unit comprises at least one of an SLO imaging function or an OCT imaging function.

5. The optical system according to claim 1, wherein the positive lens has a convex surface facing toward the concave reflector and a substantially plane surface facing toward the first and second scanners.

6. The optical system according to claim 1, wherein said catadioptric afocal relay system includes a positive lens spatially disposed between the two scanners and the concave mirror, the positive lens having a convex surface facing toward the concave reflector and a substantially plane surface facing toward the first and second scanners.

7. An optical system configured for imaging an object with the use of two independently-scanning reflectors, the optical system having an optical axis and comprising:
    first and second scanning reflectors, the first scanning reflector being configured to scan a beam of light incident thereon in a first plane, the second scanning reflector being configured to scan a beam of light incident thereon in a second plane, and the first and second planes being orthogonal to one another; and
    a catadioptric afocal relay system disposed along the optical axis in optical communication with, and between, the first and second scanning reflectors,
    wherein:
said catadioptric afocal relay system is configured to image one of the first or second scanning reflectors onto another of the first or second scanning reflectors, in light propagating along the optical axis, with a unit magnification, and said catadioptric afocal relay system includes a concave mirror for reflecting a scanned light beam from said one of the first or second scanners and guiding the light beam toward said other of the first or second scanners; and said concave mirror having an effective reflective region with a width that corresponds to a beam diameter of the light beam irradiated along a scanning path of the one of the first or second scanners and with a length direction of said effective reflective region corresponding to the scanning direction of the first scanner or the second scanner.

8. The optical system according to claim 7, an operation of which in light at wavelengths within a pre-determined spectral range being characterized by a first Strehl ratio at a central wavelength of the spectral range, the first Strehl ratio exceeding 0.96.

9. The optical system according to claim 7, an operation of which in light at wavelengths within a pre-determined spectral range being characterized by a Strehl ratio exceeding 0.96 for any field height in a range from −20 degrees to +20 degrees with respect to the optical axis.

10. The optical system according to claim 9, in which a Strehl ratio corresponding to an absolute value of a field height of 20 degrees is not smaller than 0.978 at a central wavelength of said spectral range.

11. The optical system according to claim 7, an operation of which in light at wavelengths within a pre-determined spectral range being characterized by ray aberrations not exceeding 0.25 milliradians for any field height value between first and second values of the field height.

12. The optical system according to claim 7, wherein the concave mirror of said catadioptric afocal relay system having a radius of curvature that remains constant at any point across the reflector.

13. The optical system according to claim 7, wherein said width of said effective reflective region at said reflective surface of said concave reflector is from two times to ten times said beam diameter.

* * * * *